(12) United States Patent
Morgan et al.

(10) Patent No.: US 11,569,568 B2
(45) Date of Patent: Jan. 31, 2023

(54) WEARABLE ANTENNA AND INTRA-UTERINE MONITORING SYSTEM

(71) Applicant: University of Southampton, Southampton (GB)

(72) Inventors: Hywel Morgan, Wiltshire (GB); Shilong Lu, Southampton (GB); Ying Cheong, Southampton (GB)

(73) Assignee: UNIVERSITY OF SOUTHAMPTON, Southampton (GB)

( * ) Notice: Subject to any disclaimer, the term of this patent is extended or adjusted under 35 U.S.C. 154(b) by 241 days.

(21) Appl. No.: 16/635,410

(22) PCT Filed: Aug. 1, 2018

(86) PCT No.: PCT/GB2018/052207
§ 371 (c)(1),
(2) Date: Jan. 30, 2020

(87) PCT Pub. No.: WO2019/025802
PCT Pub. Date: Feb. 7, 2019

(65) Prior Publication Data
US 2021/0098865 A1  Apr. 1, 2021

(30) Foreign Application Priority Data
Aug. 1, 2017 (GB) .................................... 1712326

(51) Int. Cl.
*H01Q 1/24* (2006.01)
*H01Q 1/27* (2006.01)
(Continued)

(52) U.S. Cl.
CPC ........... *H01Q 1/273* (2013.01); *A61B 5/0031* (2013.01); *A61B 5/4325* (2013.01); *H01Q 7/00* (2013.01)

(58) Field of Classification Search
CPC ...... A41D 1/002; A41D 1/21; A41D 2500/10; A41D 2500/20; A61B 2562/0204;
(Continued)

(56) References Cited

U.S. PATENT DOCUMENTS 5,431,171 A  7/1995  Harrison et al.
6,951,536 B2  10/2005  Yokoi et al.
(Continued)

FOREIGN PATENT DOCUMENTS

| CN | 1734833 A | 2/2006 |
| EP | 1260176 A2 | 11/2002 |
| WO | 2015082987 A1 | 6/2015 |

OTHER PUBLICATIONS

International Search Report and Written Opinion for International Patent Application No. PCT/GB2018/052207, dated Jan. 9, 2019, 12 pages.

*Primary Examiner* — Linh V Nguyen
(74) *Attorney, Agent, or Firm* — Armstrong Teasdale LLP

(57) ABSTRACT

A wearable antenna is described, for wirelessly receiving sensor data generated by an implantable sensor device implanted in a uterus, the wearable antenna, in use, extending around the waist of the wearer's body, and having a downwardly extending portion for location at the front of the wearer's body. In this way, an improved electromagnetic interaction between the wearable antenna and the implantable sensor can be achieved. Further, the wearable antenna may have an undulating shape around at least a portion of the wearer's waist, to permit expansion and contraction of the wearable antenna about the wearer's waist.

19 Claims, 9 Drawing Sheets

(51) Int. Cl.
*A61B 5/00* (2006.01)
*H01Q 7/00* (2006.01)

(58) Field of Classification Search
CPC ... A61B 5/282; A61B 5/4356; A61B 5/02411; A61B 5/0002; A61B 5/6823; A61B 5/344; A61B 5/6804; A61B 5/7203; A61B 1/00016; A61B 1/041; A61B 2503/02; A61B 2562/0209; A61B 5/0006; A61B 2562/04; A61B 2562/0219; A61B 5/0011; A61B 5/002; A61B 5/0022; A61B 5/0024; A61B 5/01; A61B 5/02055; A61B 5/021
USPC .......................... 343/702, 700 MS; 600/424
See application file for complete search history.

(56) References Cited

U.S. PATENT DOCUMENTS

| | | |
|---|---|---|
| 10,039,459 B2 | 8/2018 | Oz et al. |
| 2002/0173718 A1* | 11/2002 | Frisch .................... A61B 5/073 600/424 |
| 2009/0292182 A1* | 11/2009 | Horn ...................... A61B 5/064 600/593 |
| 2011/0083673 A1* | 4/2011 | Swann .................... A61F 6/225 128/831 |
| 2012/0035508 A1* | 2/2012 | Van Leer ............. A61B 5/4356 600/588 |
| 2013/0038493 A1 | 2/2013 | Druyan et al. |
| 2014/0065107 A1* | 3/2014 | Lockwood ......... A61K 38/4893 514/17.7 |
| 2015/0048981 A1 | 2/2015 | Choi et al. |
| 2016/0000374 A1* | 1/2016 | Dandekar ............. A61B 90/98 600/587 |
| 2016/0128594 A1* | 5/2016 | Amir ..................... A61B 5/746 600/382 |
| 2016/0317091 A1* | 11/2016 | Olukoya ............ A61B 5/4356 |
| 2017/0095667 A1 | 4/2017 | Yakovlev et al. |
| 2017/0265807 A1* | 9/2017 | Stopek ..................... A61B 5/01 |
| 2019/0076033 A1* | 3/2019 | Sweeney ................ G16H 40/63 |
| 2019/0200916 A1* | 7/2019 | Hyde .................... A61B 5/7214 |
| 2020/0093375 A1* | 3/2020 | Tseng .................. A61B 5/6832 |
| 2020/0335274 A1* | 10/2020 | Lu ........................ H04B 5/0031 |

\* cited by examiner

Elastic region

Elastic region

WEARABLE ANTENNA AND INTRA-UTERINE MONITORING SYSTEM

CROSS-REFERENCE TO RELATED APPLICATIONS

This application is the 35 U.S.C. § 371 national phase of International Patent Application No. PCT/GB2018/052207, filed Aug. 1, 2018, which claims priority to Great Britain Patent Application No. 1712326.6, filed Aug. 1, 2017, both of which are incorporated herein by reference in their entirety.

TECHNICAL FIELD

The present invention relates to a wearable antenna, and to an intra-uterine monitoring system comprising such a wearable antenna. Embodiments of the present invention relate to a system for long-term, real-time, in-vivo measurement of biophysical parameters in a human uterus.

BACKGROUND

More than 30% of all human conceptions do not advance beyond 20 weeks of gestation. One in six couples suffer from infertility, and in around 25% of couples no clear reason is identified. Even after assistance from artificial reproductive technologies, take home baby rates have altered little in the last five to ten years. This may reflect the lack of understanding of the pathophysiological mechanisms and clinically relevant diagnostic approaches for interrogating uterine functions. An interaction between the intra-uterine environment (biophysical parameters, such as temperature, dissolved oxygen concentration and pH) and reproductive health is likely, but very little is known about the biophysical characteristics of the uterus and how they alter through the menstrual cycle. The available data is mostly derived from snapshot technology and wired sensor probes, both of which do not enable real-time long-term in-vivo monitoring.

In a previous patent application by the present Applicant, an intra-uterine monitoring system is described which addresses some of the limitations of the prior art.

Part of such an intra-uterine monitoring system is a wearable receiver device which is required to wirelessly communicate with (and preferably provide power to) a sensor device implanted within the uterus. The wearable receiver has a primary coil which generates a magnetic field, which interacts with a secondary coil of the implanted sensor. Efficient and effective data communication and power transfer is a function of, among other things, the relative positions and geometries of the primary and secondary coils. While the orientation of the secondary coil of the implanted sensor can be controlled, its location is relatively constrained by its position within the uterus. Further, as will be explained below, the uterus is not identically positioned and oriented in all women, nor identically positioned and oriented within the same women at different times.

In a wireless energy transfer and communication system of this type, especially for intrauterine environment monitoring applications, data drop-out may occur because of a mismatch between the two (primary and secondary) antennas which results in insufficient energy being delivered to the implantable sensor for the measurement to take place, or because the acquired sensor data cannot be delivered from the implantable sensor to the wearable device.

There are also issues associated with wearing a loop antenna, which may be uncomfortable and unfriendly for the user. For example, the wearing of a loop antenna may limit the user's normal activity and risk the antenna being broken.

The present invention is intended to address certain of these limitations.

SUMMARY OF THE INVENTION

According to a first aspect of the present invention, there is provided a wearable antenna, for wirelessly receiving sensor data generated by an implantable sensor device implanted in a uterus, the wearable antenna, in use, extending around the waist of the wearer's body, and having a downwardly extending portion for location at the front of the wearer's body. In this way, an improved electromagnetic interaction between the wearable antenna and the implantable sensor can be achieved.

When the wearable antenna is worn, the downwardly extending portion preferably extends downwards from the wearer's waist towards their groin. The downwardly extending portion may extend to a position at or below the horizontal position of the uterus. The downwardly extending portion may be a single curve. A further downwardly extending portion may be provided for location at the rear of the wearer's body (that is, at the opposite side of the antenna to the downwardly extending portion adjacent the wearer's groin).

According to a second aspect of the invention, there is provided a wearable receiver device comprising a wearable antenna according to the above. The wearable receiver device may be a belt, or an undergarment.

At least a portion of the wearable receiver device may be elasticated, to permit expansion and contraction about the wearer's waist. The wearable receiver device may comprise one or more elasticated regions and one or more substantially inelastic regions, the shape of the antenna being permitted to deform only in the elasticated regions as the wearable receiver device is stretched.

The antenna may have an undulating shape within at least the elasticated portions of the wearable receiver device. The undulating shape may be substantially sinusoidal, or take an alternative waveform pattern.

The wearable receiver device may comprise a control unit containing transceiver circuitry and a power source, for transmitting electrical power from the antenna of the wearable receiver device to an antenna of the implantable sensor device, and for receiving sensor data from the implantable sensor device, via electromagnetic coupling. The control unit may be operable to transmit control signals to the implantable sensor device via the electromagnetic coupling. The control unit is preferably detachable from the wearable receiver device. In this case, the wearable receiver device may be washable when the control unit is detached.

The wearable receiver device may comprise a buckle, for mechanically securing the belt about the wearer's waist, and a connector, for completing an antenna circuit about the wearer's waist. The buckle may permit size adjustment of the belt.

According to a third aspect of the present invention, there is provided an intra-uterine monitoring system, comprising:
 an implantable sensor device for implantation in a uterus for measuring conditions within the uterus to generate sensor data; and
 a wearable antenna, for wirelessly receiving the sensor data generated by the implantable sensor device;

wherein the wearable antenna, in use, extends around the waist of the wearer's body, and has a downwardly extending portion at a part of the receiver device for location at the front of the wearer's body.

The antenna may be operable to transmit electrical power to the implantable sensor device via electromagnetic coupling.

According to a fourth aspect of the present invention, there is provided a wearable antenna, for wirelessly receiving sensor data generated by an implantable sensor device implanted in a uterus, the antenna, in use, extending around the waist of the wearer's body, and having an undulating shape around at least a portion of the wearer's waist, to permit expansion and contraction of the wearable antenna about the wearer's waist.

The undulating shape may be substantially sinusoidal, or take an alternative waveform pattern. Preferably, the undulating shape is provided, when worn, to one or both sides of the user's body, to seek to minimise disruption to the electromagnetic interaction between the wearable antenna and the implantable sensor.

According to a fifth aspect of the present invention, there is provided a wearable receiver device comprising an antenna according to the above, wherein the wearable receiver device comprises one or more elasticated regions and one or more substantially inelastic regions, the shape of the antenna being permitted to deform only in the elasticated regions as the wearable receiver device is stretched. The antenna preferably has the undulating shape within at least elasticated portions of the wearable receiver device.

According to a sixth aspect of the present invention, there is provided a intra-uterine monitoring system, comprising:
an implantable sensor device for implantation in a uterus for measuring conditions within the uterus to generate sensor data; and
a wearable antenna, for wirelessly receiving the sensor data generated by the implantable sensor device;
wherein the wearable antenna, in use, extends around the waist of the wearer's body, and has an undulating shape around at least a portion of the wearer's waist, to permit expansion and contraction of the wearable receiver device about the wearer's waist.

Embodiments of the present invention may provide a more reliable and robust belt coil design, and can achieve better wireless performance and a wider working angle for interacting with an implanted sensor device.

Within the present application, the terms antenna and coil are used interchangeably. Two antennae, or coils, are used in the present technique. The first of these (primary) is part of a wearable receiver device, and forms one or more complete circuits of conducting wire extending about the receiver device (and consequently about the wearer's body). The second of these (secondary) is part of an implantable sensor device, and may take the forms for a coil or loop antenna, for example in the form of a solenoid coil. In embodiments, electrical power is provided from the primary coil/antenna to the secondary coil/antenna to power the implantable sensor device. Data signals are transmitted from the secondary antenna/coil to the primary antenna/coil in order that sensor data can be exported from the implantable device to outside of the body, and in some embodiments control (command) signals may be transmitted from the primary antenna/coil to the secondary antenna/coil to allow control of the implantable sensor device in situ. In such cases, both electrical power transfer and bidirectional communication is provided between the wearable receiver device and the implantable sensor device by way of electromagnetic coupling between the primary and secondary antennae/coils. The present techniques seek to improve this electromagnetic coupling which providing a wearable device which is robust, comfortable and user friendly.

BRIEF DESCRIPTION OF THE DRAWINGS

Embodiments of the present invention will now be described by way of example only with reference to the accompanying drawings where like parts are provided with corresponding reference numerals and in which.

DETAILED DESCRIPTION

Figure 1:
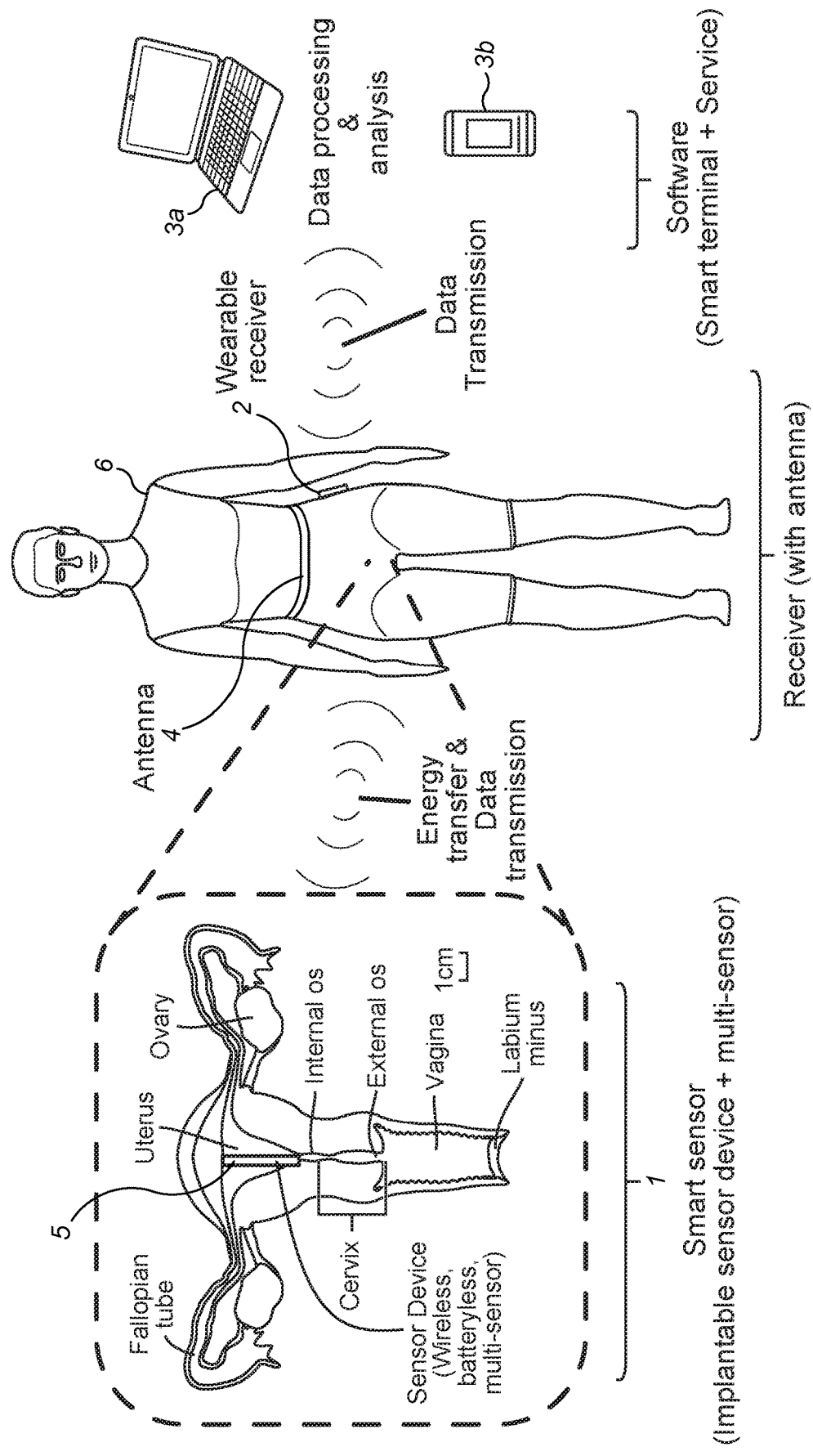
FIG. 1 schematically illustrates an intra-uterine monitoring system according to one embodiment.

Referring to FIG. 1, a three-module structured multi-parameter in-vivo sensing platform for intra-uterine environment monitoring is shown. The platform comprises a smart sensor 1 (implantable sensor device, which is suitably shaped and dimensioned for implantation in a human uterus), an external, generally wearable, receiver 2 and monitoring software installed on suitable data processing hardware, such as a computer 3a or portable electronic device 3b. The smart sensor 1 is a fully implantable (within the uterus 5 of a human female body 6) sensor device incorporating multiple embedded biosensors (intended for measuring temperature, dissolved oxygen concentration (DOC) and pH). Temperature, DOC and pH are considered to be the three most important parameters to measure for this application because they maintain a homeostatic controlled balance of gases and acid-base which is vital to human life and reproduction. They are likely to determine the receptivity of the intra-uterine environment to an implanting embryo.

The smart sensor 1 is capable of wirelessly receiving power from and wirelessly transmitting data to the wearable receiver 2 which is located outside the body of a user, and worn by the user. As a result, the smart sensor 1 dispenses with the need for a battery and cables, and is of comparable size to the widely-used IUDs (intra-uterine devices) for contraception. This is important, because for implantation in the uterus, a device must meet strict size limits. Compared with intra-uterine devices (IUDs) widely used for contraception, battery-based sensors have been found to be too large to be used in the uterus. Moreover, designs based on a battery typically have limitations due to the physical size of the battery and short lifetime before the battery is too depleted to continue operating. Furthermore, there are potential risks from the toxic material of batteries.

The receiver 2 serves as a medium between the implantable sensor device 1 and the external data processing device running suitable software (and thus operating as a data analyser). In particular, the receiver 2 delivers energy to the sensor device and collects real-time information. An antenna 4 of the receiver 2 can be embedded into clothing and wired to the receiver 2. The software module is developed for in-vivo data uploading simultaneously to smart terminals or PC servers for post data processing and analysis. The software module consists of a set of monitoring software running on a PC or smart terminal which is designed to be a friendly user interface for data processing and system configuration. The positioning of the smart sensor 1 within the uterus is shown in FIG. 1. In particular, the smart sensor 1, which may typically have a generally elongate structure, is positioned substantially upright (vertical) within the uterus. As a result, the longitudinal axis of the smart sensor 1 is substantially vertical when the user is standing.

In this three-module structured system, the effectiveness of the wireless energy transfer and data communication between the smart sensor 1 and receiver 2 directly affect the usability of the intended system. An optimised design may not only result in better performance, smaller size, low power consumption and lower cost, but also improve end-user experience and clinical practise.

Figure 2:
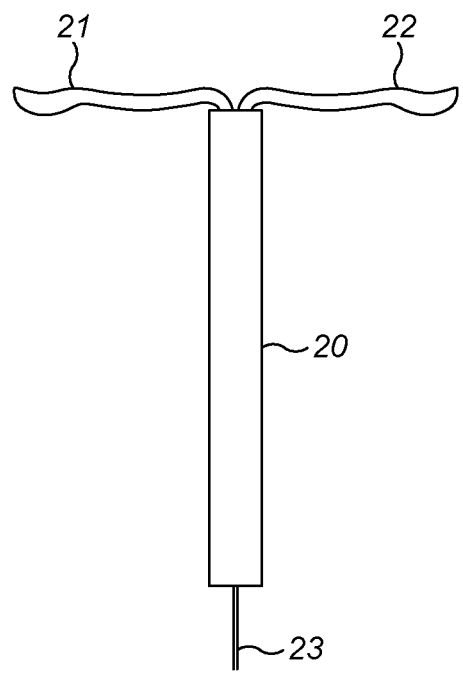
FIG. 2 schematically illustrates an implantable sensor device according to one embodiment.

Referring to FIG. 2, an example structure for the smart sensor 1 is shown. In FIG. 2, a T-type smart sensor can be seen to comprise a body 20, a first arm 21, and a second arm 22. Once inserted into the uterus, the first and second arms 21, 22 help to retain the smart sensor 1 in place within the uterus. While in the present embodiment two arms are used, it should be understood that in other embodiments a single arm could be used, or more than two arms could be used. The body 20 may comprise a main circuit board (not shown) and an antenna (also not shown). Alternatively, the antenna may be fixed on the second arm 22. The main circuit board carries the sensors and the circuitry for temporarily storing electrical energy, controlling the smart sensor 1 in acquiring sensor data, and in transmitting the acquired sensor data to the wearable receiver device.

The sensor device orientation is vertical in the uterus, making it suitable for use with a receiver having a belt antenna or an antenna embedded in underwear. A cord 23 is used to assist with removal of the device from the uterus.

Figure 3:
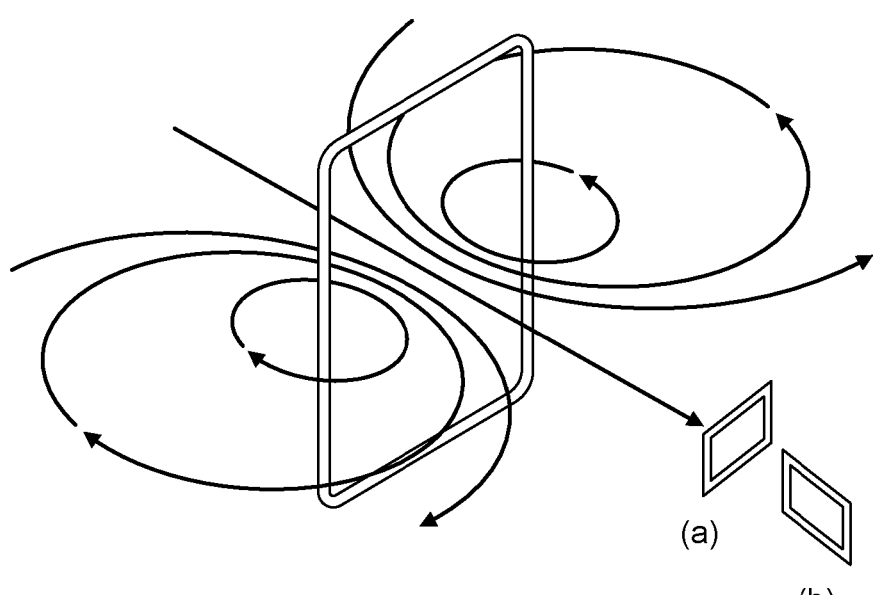
FIG. 3 schematically illustrates the principle of electromagnetic coupling between primary and secondary coils.

Electromagnetic induction wireless transmission technology is used for near field energy transfer through the use of two coupled coils, primary and secondary coils. FIG. 3 schematically illustrates this, showing two possible orientations of a secondary coil (small coil) with respect to a primary coil (large coil). One of these orientations, denoted as (a) in FIG. 3, shows the plane of the secondary coil being parallel to the plane of the primary coil—this being the best angle for electromagnetic coupling between the two coils. The other orientation, denoted as (b) in FIG. 3, shows the plane of the secondary coil being perpendicular to the plane of the primary coil—this being the worst angle for electromagnetic coupling between the two coils. As explained above, for the intrauterine environment monitoring application, the primary coil is the belt antenna and the secondary coil is the implantable sensor antenna in the uterus. The electric current flowing through the primary coil creates a magnetic field that acts on the secondary coil producing an induced current within it. Tight coupling is beneficial for high energy harvest efficiency and long working distance. Increasing the distance between the primary and secondary coils results in the magnetic field extending beyond the secondary coil receiving area and leads to a loss of transmitted energy. Generally speaking, to the same secondary coil, more flux going through the cross area of the secondary coil results in more energy being delivered. Women's uteri vary in orientation and move in different circumstances such as in dependence on whether the bladder is full or empty. This means that it can be difficult to always achieve idea transmission conditions, as movement of either the belt or the uterus results in a relative orientation between the primary and secondary coils which is not always ideal.

One aspect of the present technique seeks to shorten the distance between the primary and secondary coils and offer a good orientation of the secondary coil to the primary coil, which can achieve better energy transfer efficiency and lower data drop rate.

Figure 4:
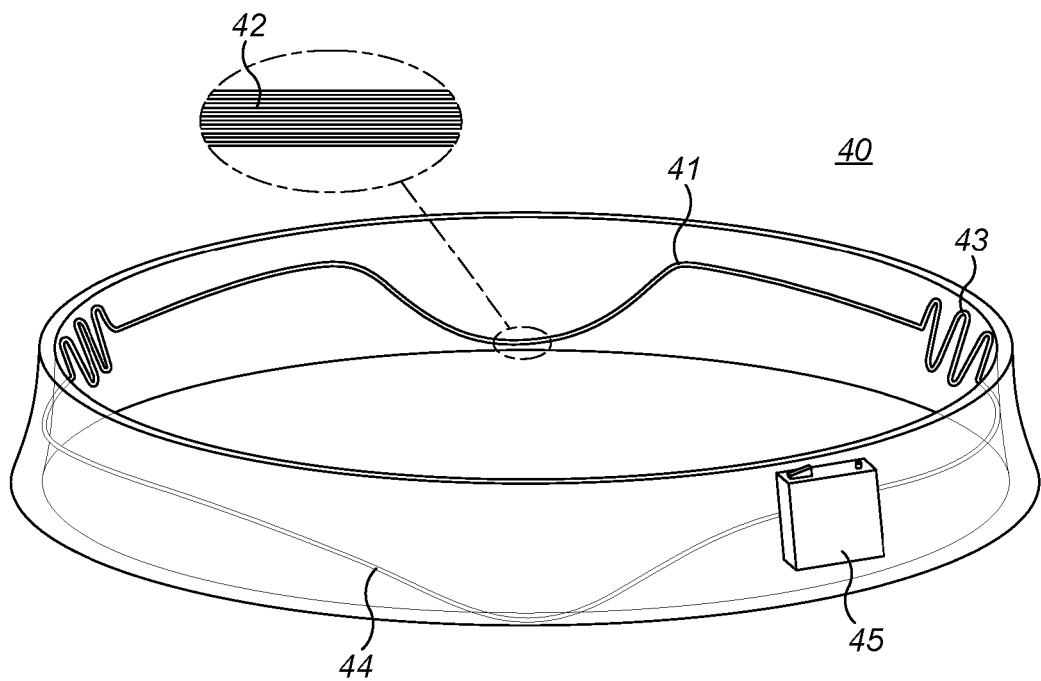
FIG. 4 schematically illustrates a wearable receiver device according to a first embodiment.

Referring to FIG. 4, a belt 40 is provided as a wearable receiver device, and comprises a complete coil 41 which extends around the belt, and which has a length longer than an intended waist size. The coil 41 is embedded within a partially elastic belt structure, which may be a composite structure of fabric panels and elastic supports, or may be a simple elastic material structure. The user is required to pass the belt 40 over their head, or over their feet in order to wear it, since the belt forms a continuous loop. The coil 41 comprises several turns (that is, a continuous current path extends about the belt a plurality of times), as shown close up at 42. The coil 41 may extend in a generally linear manner about a substantial portion of the belt, with the exception of at first and second extendable regions 43 which are intended to be located to the side of the wearer, and a downwardly extending region 44 intended to be located to the front of the wearer. In this embodiment, a further downwardly extending region is provided opposite the region 44, to the rear of the wearer. A reader device 45 is removably mounted to the belt 40. Various forms of removable mounting could be used, such as clips, brackets, complementary male and female formations, Velcro™ or magnets. The belt is washable, once the reader device 45 has been removed. The extendable regions 43 comprise a coil wiggle to permit elasticity. The belt itself is preferably elastic only within the extendable regions 43, since expansion of the belt elsewhere may result in stresses on the linear parts of the coil, leading to damage. The downwardly extending region 44 may extend downwardly to a certain level of groin contour which is preferably slightly lower than the uterus on the horizontal plane (by a few cm). The downwardly extending region to the rear of the belt/wearer may be smaller, for example extending downwardly by only a few cm.

Figure 5:
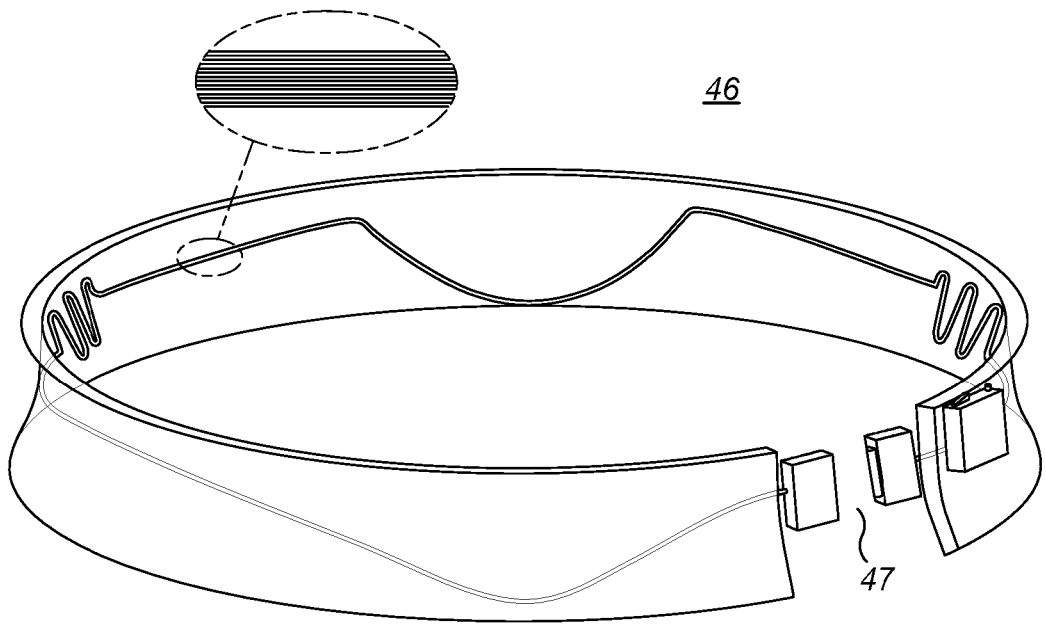
FIG. 5 schematically illustrates a wearable receiver device according to a second embodiment.

Referring to FIG. 5, an alternative wearable receiver belt device 46 is shown. This is similar to the belt 40 of FIG. 4, but comprises an openable/breakable coil having wires which join together through a multi-pin connector 47. The belt 46 can be used as normal belt, in which the wearer places the belt around their waist and closes the multi-pin connector 47, with the result that a complete loop coil is formed up (which will have multiple turns, as described in relation to FIG. 4). It will be understood that the belt 46 is both mechanically and electrically connected into a continuous loop by way of the connector 47. The belt 46 of FIG. 5 may be more convenient for the wearer to use than the belt 40 of FIG. 4, but at the cost of a potential failure mode via the connector 47.

Figure 6:
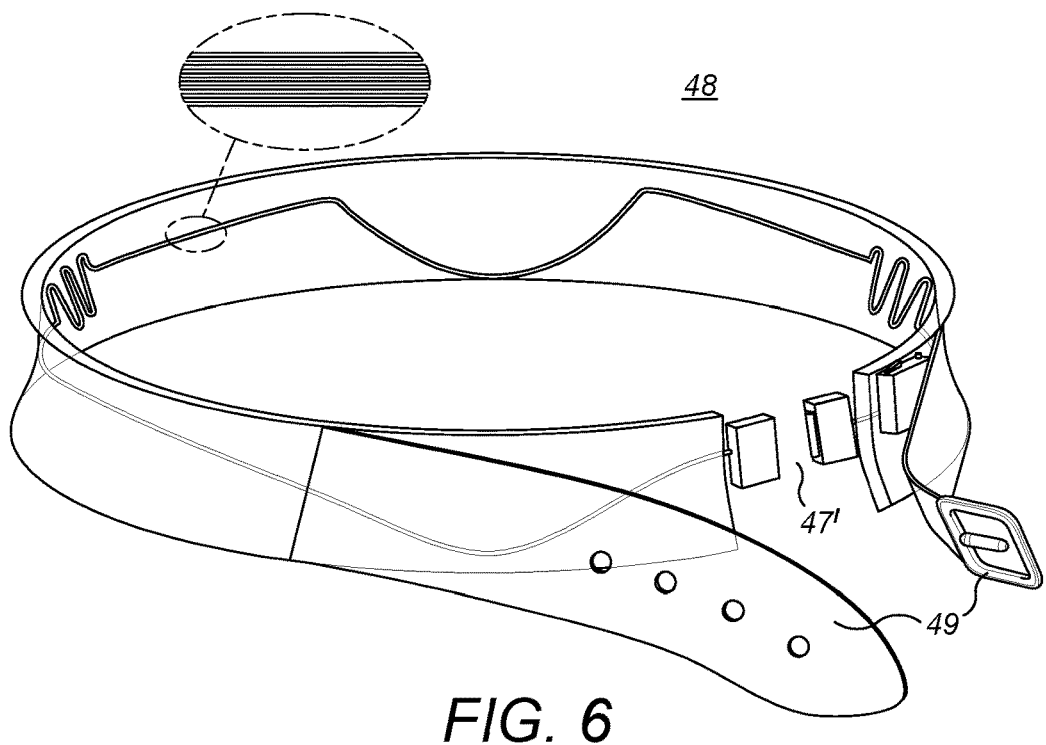
FIG. 6 schematically illustrates a wearable receiver device according to a third embodiment.

Referring to FIG. 6, another alternative wearable receiver device 48 is shown, again utilising an openable/breakable coil. This is similar to the belt 46 of FIG. 5, since it utilises an electrical connector to break/unbreak the circuit by virtue of the wires of the coil join together through a multi-pin connector 47'. However, in the case of the belt 48 of FIG. 6, an additional belt buckle 49 is provided over the top of the multi-pin connector 47', making it possible to adjust the size of the belt to match the wearer's waist size. In this case, the connector 47' is required to provide the electrical connection, whereas the buckle 49 provides the mechanical connection, and adjustability of the size of the belt 48. The electrical connector 47' is protected by the buckle 49 due to the location of the buckle over the top of the connector 47'.

Each of the embodiments of FIGS. 4, 5 and 6 provides a flexible elastic antenna designed to be worn around the waist. This is because, considering a user's comfort and normal activity, a simple loop antenna would not be suitable for this use. Accordingly, the antenna coil is embedded on an elastic band which can fit a range of waist sizes, and contend with distortion associated with normal activity, such as breathing and moving. The elasticity and flexibility is beneficial even for the FIGS. 5 and 6 designs in which the belt can be put on and taken off by breaking the circuit with a connector 47/47'.

It will be appreciated that the complete coil has a circumference longer than the intended waist line. To preserve the shape of the coil (which will affect the magnetic field generated by the belt coil), around 80% of the coil may be fixed onto the belt with no relative movement when the belt is stretched. The flexible part is provided in the excessive coil stored in the shape of a sine-wave or other preferably undulating shape. If the elastic belt cannot hold itself in place without tightening too much on the user, additional common belt buckle (cannot be made of ferromagnetic material) can be used on top of the elastic region, to provide extra support for the weight of batteries and circuits which are integrated onto the belt.

The belts 40, 46, 48 described above in relation to FIGS. 4, 5 and 6 in all cases carry reader electronics 45 and have a coil 41 integrated therein. The belts 40, 46 and 48 are flexible and elastic, which make them user friendly for daily use over the course of the monitoring period. Their position with respect to the wearer's body, and thus the implanted sensor device, is secured during monitoring, either by the elasticity of the belt and/or by the mechanical connection provided by the connector 47 of FIG. 5 or the buckle 49 of FIG. 6. As the belt 40, 46 and 49 is to be worn over an extended period (for example one month), it may become soiled, and it is therefore washable after disconnecting the reader electronics 45. The antenna pattern of the coil 41 is specially designed for better electromagnetic field distribution and wireless performance, as will be discussed in more detail below.

Figure 7:
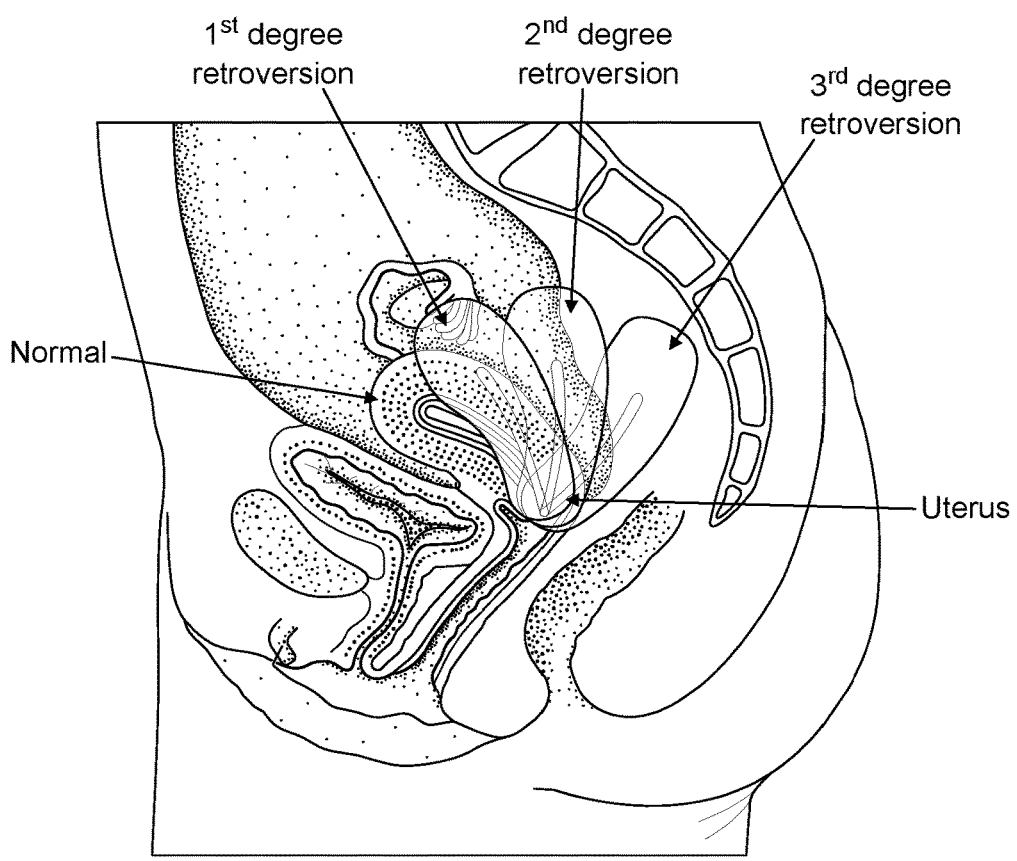
FIG. 7 schematically illustrates a variety of uterus positions to be catered for by embodiments of the present invention.

Referring to FIG. 7, a variety of different positions of the human uterus are shown. In particular, a normal uterus position is shown, as well as a uterus in $1^{st}$ degree, $2^{nd}$ degree and $3^{rd}$ degree retroversions. It will be appreciated that the different positions of the uterus, which may vary between individuals and also within a given individual over time is dependent on, for example, how full their bladder is, may give rise to differences in position and/or orientation of the implantable sensor device when in situ.

Figure 8:
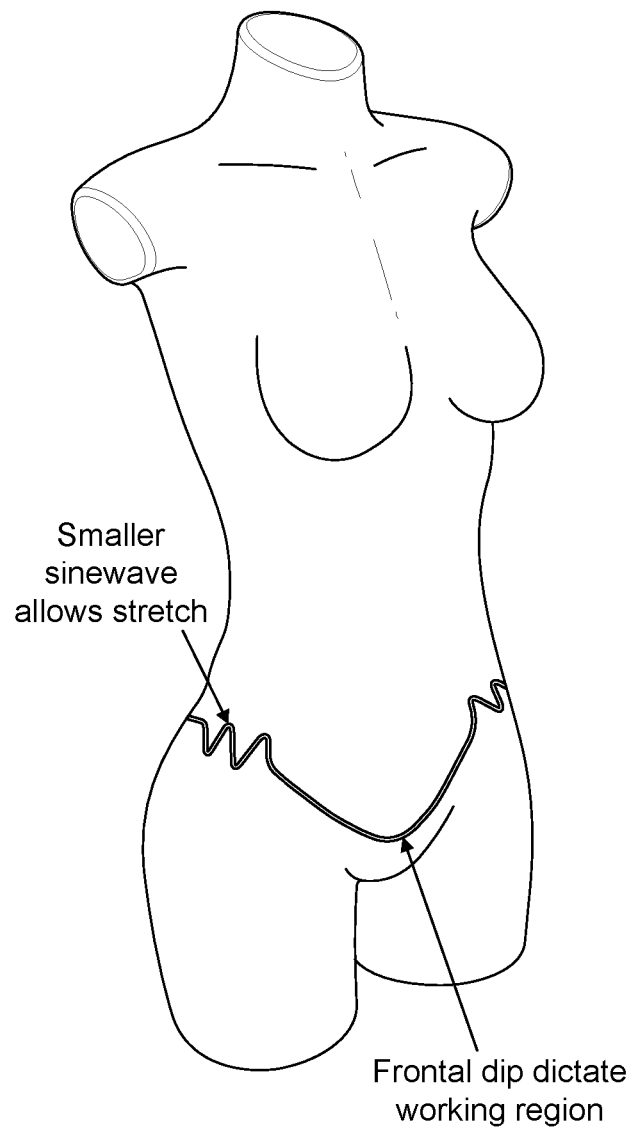
FIG. 8 schematically illustrates a coil structure according to an embodiment of the present invention.

Referring to FIG. 8, the configuration of the primary coil of the wearable receiver device is shown with respect to a human body in the position it would be located if embedded within a belt in the manner shown in FIGS. 4 to 6 above. In the interests of clarity the belt itself is omitted from FIG. 8. It can be seen that the primary coil has a frontal dip which extends down towards the wearer's groin and which partially dictates the working region within the human body within which the primary coil can interact with a secondary coil. When the belt is worn, the frontal dip extends downwardly along the contour of the groin (that is, inwardly of the belt) to a position which is slightly lower (by a few cm) than the uterus on the horizontal plane (when the wearer is stood upright). The primary coil also has a smaller sine wave pattern to either side of the wearer's body, permitting expansion of the coil to handle different waste sizes, movement of the body, and/or assist with the belt being put on and taken off in the case of the FIG. 4 belt. The sine wave pattern need in practice not be sine wave shaped, but may have any non-linear form (generally undulating) which can be straightened out to extend the effective length of the antenna. Sawtooth or square wave patterns are viable, but the sharp changes in direction form weak points in the wires, and so gentle curves are preferable. Each sine wave pattern is co-located with an elasticated portion of the belt, to permit the belt and the coil to expand and contract together. The coil is levelled at the top of the leg to provide clearance for leg motion.

Generally, two benefits from the downwardly curved frontal portion of the coil can be identified. Firstly, this shortens the distance between the belt antenna and the implanted sensor in the uterus, and offers a good orientation of the sensor antenna to the belt antenna. Secondly, it manipulates the field distribution and provides stronger field/high flux density in a portion of the human body where the uterus is expected to be found (generally centrally disposed between the left hand side and right hand side of the body, but at any of a range of positions between the front and rear of the body). More generally, the frontal dip influences whether the implanted device would receive enough power for certain body stances.

Figure 9:
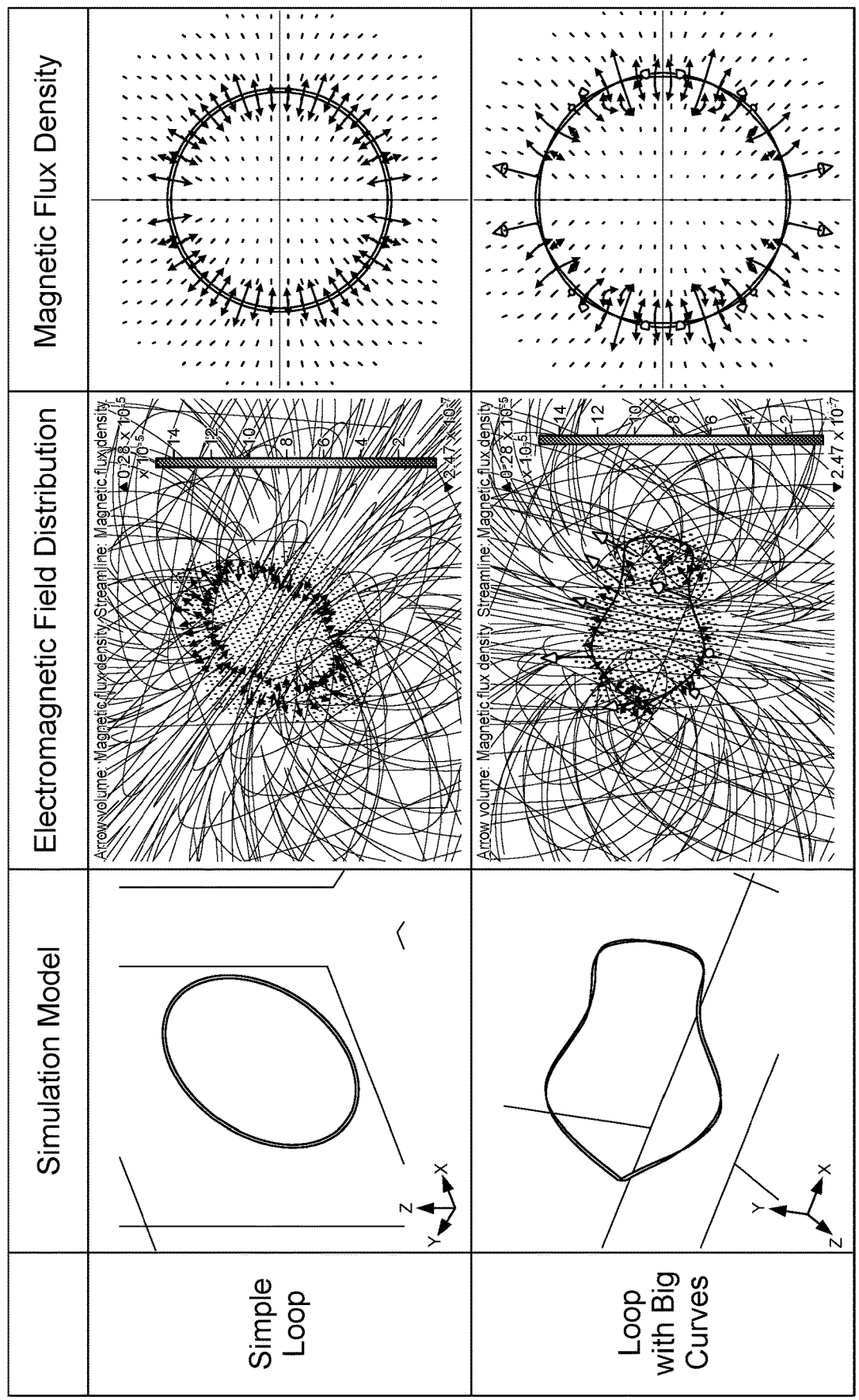
FIG. 9 schematically illustrates the effect of modifying the shape of a simple loop antenna on the resulting field distribution and flux.

It will therefore be appreciated that the large downward curve in the coil at the front of the belt compensates for variations in the position of the implantable device in the body, as well as shortening the distance between the belt antenna and the implanted sensor in the uterus, generally offering a good orientation of the sensor antenna to the belt antenna, and manipulating the field distribution to achieve stronger field/high flux density in areas where the uterus can be expected to be present. FIG. 9 shows a comparison between a simple (circular) loop antenna and a loop with large curves. A simulation model was defined for each structure (the shape being shown in the column "Simulation model"), and used to generate a corresponding electromagnetic field distribution and magnetic flux density. The magnitude of the field strength and flux density are represented by the size of the arrows. It can be seen that, while the simple loop antenna gives rise to a relatively uniform (in magnitude and orientation) distribution, the modified loop antenna with large curves gives rise to a less uniform distribution, and in particular one in which the direction and magnitude of the field and flux can be tailored into certain regions and orientations. It will be appreciated that this principle can be used to tailor the electromagnetic field generated by the belt antenna by defining the shape of the belt antenna appropriately. In particular, the electromagnetic field can be shaped so as to optimise the interaction between the belt antenna and the implanted sensor device. It has been found that the frontal dip, optionally in combination with a small rear dip, is able to achieve this distribution.

Figure 10B:
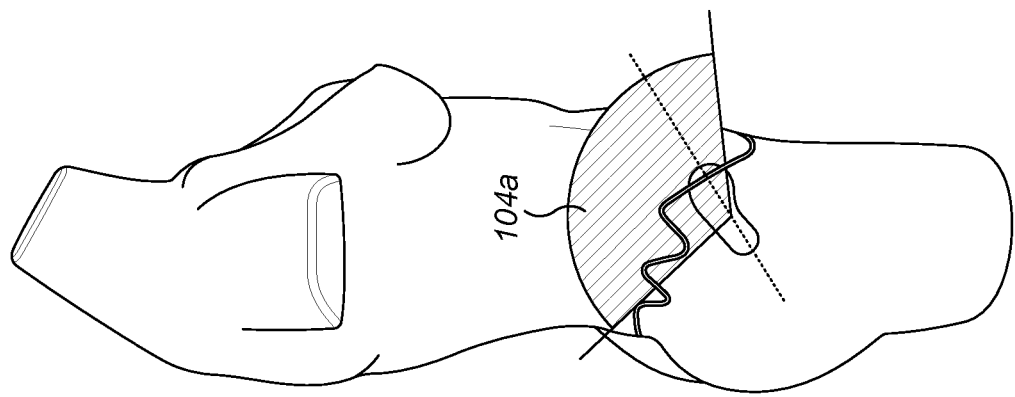
FIGS. 10A and 10B schematically illustrate working electromagnetic coupling regions achievable by a basic coil (FIG. 10A) and by embodiments of the present invention (FIG. 10B)
Figure 10A:
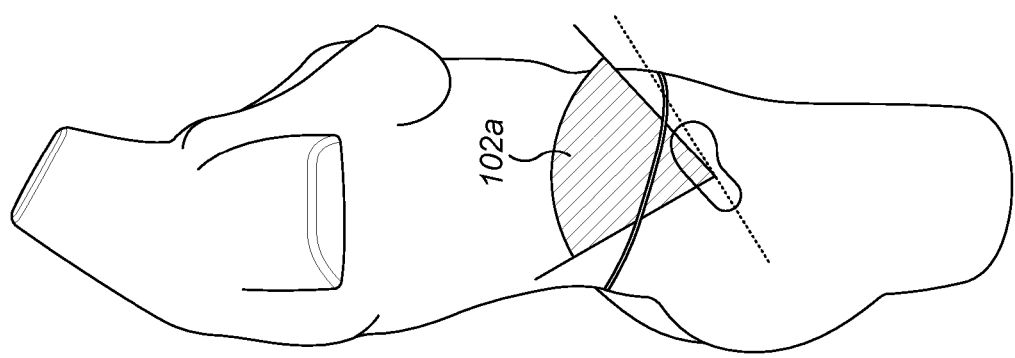

FIGS. 10A and 10B show a side view of a human body with the position of a coil antenna (the belt in which the coil is embedded is omitted from FIGS. 10A and 10B in the interests of clarity) shown. FIG. 10A shows a simple loop antenna without a frontal dip and FIG. 10B shows an antenna with a frontal dip and an undulating portion at the side of the wearer's body. In each of FIGS. 10A and 10B, a position and extent of a working area 102 (FIG. 10A) or 104 (FIG. 10B) within the human body, and with respect to the antenna is shown. It will be appreciated that the working areas 102, 104 do not have hard boundaries as suggested by FIGS. 10A and 10B, but that these areas are indicative of the area of the wearer's body in which the electromagnetic coupling between the coil antenna (primary) and the secondary coil of the implantable device can be expected to be adequate for the energy and data transfer requirements of the present application. Comparison of the working area 104 of FIG. 10B with the working area 102 of FIG. 10A, and also with the uterus positions shown in FIG. 7, reveals that the working area 104 is likely to provide good electromagnetic coupling for most uterus positions, and in particular is able to provide a larger interaction region (in a front/rear direction) than the working area 102. In other words, a stronger and more reliable interaction between the wearable antenna and the antenna of the implanted sensor device, can be achieved.

Figure 11A:
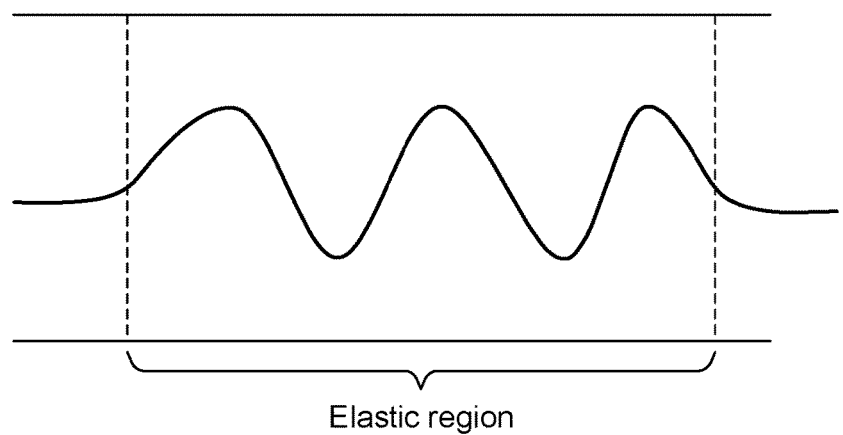
FIGS. 11A and 11B schematically illustrate a stretchable antenna region in both retracted and expanded states.
Figure 11B:
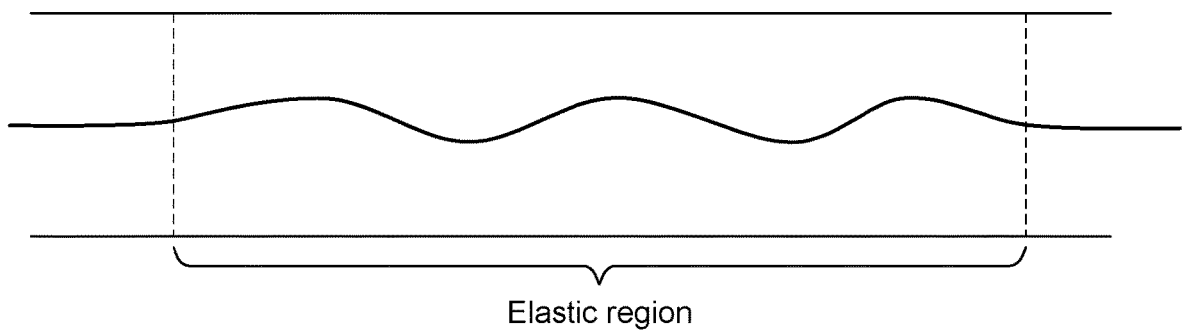

The smaller sinewave pattern provided to either side of the wearer's body provides the stretchy part of the coil. This can be seen clearly in FIG. 10B, as well as in FIGS. 4, 5, 6 and 8. When the coil is stretched to various extent, this pattern has been found to have the least effect on the electromagnetic properties of the coil, thus presenting the lowest risk in detuning the system. The smaller sinewave pattern is placed to the side of the body to improve comfort and reduce the degradation to performance. In particular, the sinewave pattern is likely to cause the electromagnetic field distribution in its vicinity to be irregular. However, by providing the sine wave to the side of the wearer's body, this disturbance is away from the central region of the wearer's body in which the implanted sensor is present (and therefore in which it is important that the electromagnetic field distribution be reliable). Referring to FIGS. 11A and 11B, the elongation of the sinewave pattern as the belt is stretched is shown. In particular, FIG. 11A shows the belt in an unstretched state, with the sinewave pattern in the coil having a relatively short wavelength with relatively short distances between adjacent peaks. The amplitude of the waveform in FIG. 11A is also relatively large. FIG. 11B shows the belt in a stretched state, with the sinewave pattern in the coil having a relatively long wavelength with relatively long distances between adjacent peaks. The amplitude of the waveform in FIG. 11B is also relatively small. It will be appreciated that the theoretical maximum stretch of the belt will correspond to the sine wave patterns being stretched out into a straight line (although it will be appreciated that this degree of stretch may be effectively forbidden by limitations in the stretch of the elastic material of which the belt itself is formed).

Figure 12:
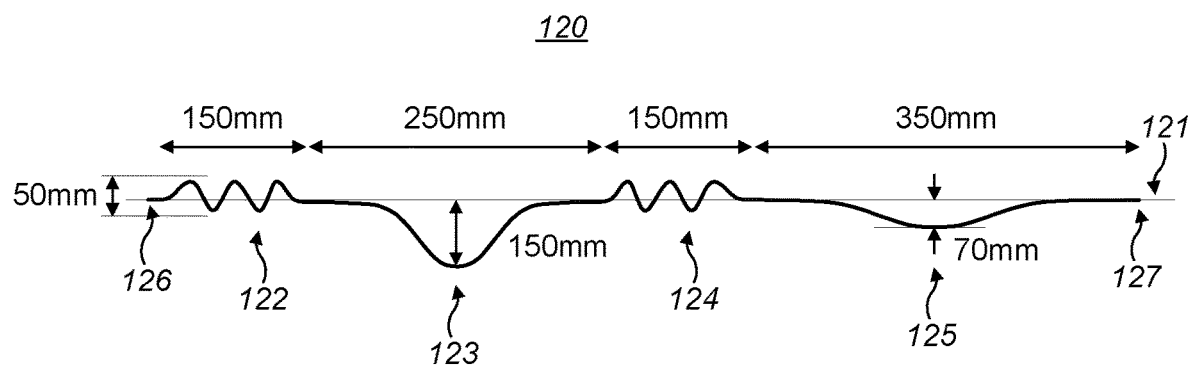
FIG. 12 schematically illustrates example dimensions of a wearable antenna.

Referring to FIG. 12, example dimensions for a wearable antenna 120 are provided. It will be appreciated that a left hand end 126 and a right hand end 127 of the antenna 120 of FIG. 12 are in practice continuous with each other (as shown in the earlier Figures), with the antenna 120 as a whole extending around the waist of a wearer as shown in FIGS. 8 and 10B. A primary plane formed by the antenna 120 is indicated by the dashed line 121. The primary plane 121 bisects the body of the wearer at or about waist height. Undulating portions 122, 124 permitting expansion of the antenna 120 are shown to extend (when in their unexpanded state) for approximately 150 mm along the antenna 120, and to have an amplitude (peak to trough) of approximately 50 mm. Accordingly, the undulations deviate upwardly and downwardly of the primary plane 121 by approximately 25 mm in either direction. It will be appreciated that different dimensions could be used while achieving the same effect. For example, the undulations 122, 124 might deviate from the primary plane 121 by an amount of between approximately 10 mm and 50 mm in either direction. A distance between the undulating formations to the front of the wearer is approximately 250 mm. A distance between the undulating formations to the rear of the wearer is approximately 350 mm. A downwardly extending portion 123 at the front of the antenna (to be worn in the vicinity of the wearer's groin area, that is to the front of the wearer) extends down for approximately 150 mm from the primary plane 121. The downwardly extending portion 123 defines a single curve. A downwardly extending portion 125 at the rear of the antenna (to be worn to the rear of the wearer) extends down for approximately 70 mm from the primary plane 121. The downwardly extending portion 125 defines a single curve, and is a shallower curve than that of the downwardly extending portion 123. Portions of the antenna 120 which are neither undulating, nor part of the downwardly extending curved portions, can be considered substantially linear portions, and these are generally coincident with the primary plane 121.

Figure 13:
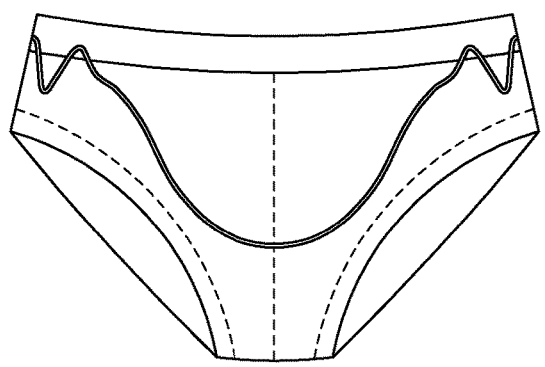
FIG. 13 schematically illustrates a coil embedded within an undergarment rather than a belt.

Referring to FIG. 13, it can be seen that the coil antenna configuration need not necessarily be applied to a belt. Instead, as shown in FIG. 12 it can be integrated into other garments, in this case underwear. The same principles apply here, in terms of the presence of a frontal dip, and the undulating portion to the side of the garment.

While the various techniques, and the implantable sensor device and external receiver have been explained in the context of intra-uterine monitoring, it will be understood that these techniques and structures could be applied to other body-cavity monitoring, such as within a vagina, bladder or digestive tract of a human or animal body.

The invention claimed is:

1. A wearable antenna, for wirelessly receiving sensor data generated by an implantable sensor device implanted in a uterus, the wearable antenna, in use, extending around the waist of the wearer's body in a continuous loop and forming a primary plane, and having substantially linear portions generally coincident with the primary plane and a downwardly extending portion defining a single curve for location at the front of the wearer's body which extends from the primary plane.

2. A wearable antenna according to claim 1, wherein, when the wearable antenna is worn, the downwardly extending portion extends downwardly from the wearer's waist towards their groin.

3. A wearable antenna according to claim 2, wherein the downwardly extending portion extends to a position at or below the horizontal position of the uterus.

4. A wearable antenna according to claim 1, having a further downwardly extending portion for location at the rear of the wearer's body.

5. A wearable receiver device comprising a wearable antenna according to claim 1.

6. A wearable receiver device according to claim 5, wherein the wearable receiver device is a belt.

7. A wearable receiver device according to claim 5, wherein the wearable receiver device is an undergarment.

8. A wearable receiver device according to claim 5, wherein at least a portion of the wearable receiver device is elasticated, to permit expansion and contraction about the wearer's waist.

9. A wearable receiver device according to claim 8, wherein the wearable receiver device comprises one or more elasticated regions and one or more substantially inelastic regions, the shape of the antenna being permitted to deform only in the elasticated regions as the wearable receiver device is stretched.

10. A wearable receiver device according to claim 8, wherein the antenna has an undulating shape within at least the elasticated portion of the wearable receiver device.

11. A wearable receiver device according to claim 10, wherein the undulating shape is substantially sinusoidal.

12. A wearable receiver device according to claim 1, comprising a control unit containing transceiver circuitry and a power source, for transmitting electrical power from the antenna of the wearable receiver device to an antenna of the implantable sensor device, and for receiving sensor data from the implantable sensor device, via electromagnetic coupling.

13. A wearable receiver device according to claim 12, wherein the control unit is operable to transmit control signals to the implantable sensor device via the electromagnetic coupling.

14. A wearable receiver device according to claim 12, wherein the control unit is detachable from the wearable receiver device.

15. A wearable receiver device according to claim 14, wherein the wearable receiver device is washable when the control unit is detached.

16. A wearable receiver device according to claim 6, comprising a buckle, for mechanically securing the belt about the wearer's waist, and a connector, for completing an antenna circuit about the wearer's waist.

17. A wearable receiver device according to claim 16, wherein the buckle permits size adjustment of the belt.

18. An intra-uterine monitoring system, comprising:
an implantable sensor device for implantation in a uterus for measuring conditions within the uterus to generate sensor data; and
a wearable antenna, for wirelessly receiving the sensor data generated by the implantable sensor device;
wherein the wearable antenna, in use, extends around the waist of the wearer's body in a continuous loop and forming a primary plane, and having substantially linear portions generally coincident with the primary plane and a downwardly extending portion for location at the front of the wearer's body which extends from the primary plane.

19. An intra-uterine monitoring system according to claim 18, wherein the antenna is operable to transmit electrical power to the implantable sensor device via electromagnetic coupling.

* * * * *